US011707469B2

(12) United States Patent
Gubler et al.

(10) Patent No.: US 11,707,469 B2
(45) Date of Patent: Jul. 25, 2023

(54) PRODUCTION OF ASPIRIN-TRIGGERED RESOLVINS WITHOUT THE USE OF ASPIRIN IN A DIETARY OMEGA-3 SUPPLEMENT

(71) Applicant: Performance Labs Pte. Ltd., Singapore (SG)

(72) Inventors: Daniel Gubler, Orem, UT (US); Michael Saunders, Orem, UT (US)

(73) Assignee: Performance Labs Pte. Ltd., Singapore (SG)

( * ) Notice: Subject to any disclaimer, the term of this patent is extended or adjusted under 35 U.S.C. 154(b) by 294 days.

(21) Appl. No.: 16/823,739

(22) Filed: Mar. 19, 2020

(65) Prior Publication Data
US 2020/0215084 A1 Jul. 9, 2020

Related U.S. Application Data

(62) Division of application No. 15/951,755, filed on Apr. 12, 2018, now Pat. No. 10,624,907.

(60) Provisional application No. 62/484,676, filed on Apr. 12, 2017.

(51) Int. Cl.
*A61K 31/618* (2006.01)
*A61K 31/198* (2006.01)
*A61P 25/04* (2006.01)
*A61K 47/12* (2006.01)
*A61K 31/355* (2006.01)

(52) U.S. Cl.
CPC .......... *A61K 31/618* (2013.01); *A61K 31/198* (2013.01); *A61K 31/355* (2013.01); *A61K 47/12* (2013.01); *A61P 25/04* (2018.01)

(58) Field of Classification Search
CPC .. A61K 31/198; A61K 31/355; A61K 31/618; A61K 47/12; A61K 2300/00; A61P 25/04
See application file for complete search history.

(56) References Cited

U.S. PATENT DOCUMENTS

| 7,341,840 B2 | 3/2008 | Serhan et al. |
|---|---|---|
| 8,586,073 B2 | 11/2013 | Drapeau et al. |
| 2006/0120975 A1 | 6/2006 | Scherl et al. |
| 2013/0195953 A1 | 8/2013 | Drapeau et al. |
| 2018/0296577 A1 | 10/2018 | Gubler |

FOREIGN PATENT DOCUMENTS

WO 2018191505 A1 10/2018

OTHER PUBLICATIONS

Arita, et al. "Stereochemical assignment, anti-inflammatory properties, and receptor for the omega-3 lipid mediator resolvin E1", J. Exp. Med., vol. 201, No. 5, Mar. 7, 2005 713-722.
Buckley, et al. "Proresolving Lipid Mediators and Mechanisms in the Resolution of Acute Inflammation" Immunity 40, Mar. 20, 2014, 315-327.
Chen, C. "COX-2's new role in inflammation" Nature Chemical Biology, vol. 6, Jun. 2010, 401-402.
Dalli, et al. "Resolvin D3 and Aspirin-Triggered Resolvin D3 Are Potent Immunoresolvents" Chemistry & Biology 20, 188-201, Feb. 21, 2013.
Groeger, et al. "Cyclooxygenase-2 generates anti-inflammatory mediators from omega-3 fatty acids" Nature Chemical Biology, vol. 6, Jun. 2010, 433-441.
Kohli "Resolvins and protectins: mediating solutions to inflammation" British Journal of Pharmacology (2009), 158, 960-971.
Lima-Garcia, et al. "The precursor of resolvin D series and aspirin-triggered resolvin D1 display anti-hyperalgesic properties in adjuvant-induced arthritis in rats" British Journal of Pharmacology (2011) 164 278-293.
Morris, et al. "Effects of Low-Dose Aspirin on Acute Inflammatory Responses in Humans" J Immunol 2009; 183:2089-2096; Jul. 13, 2009.
Ogata, et al. "Effects of aspirin-triggered resolvin D1 on peripheral blood mononuclear cells from patients with Chagas' heart disease" European Journal of Pharmacology 777 (2016) 26-32.
Olmsted, III, John "Synthesis of Aspirin—A General Chemistry Experiment" Journal of Chemical Education, Oct. 1998; vol. 75, No. 10; ProQuest p. 1261-1263.
Prescott and Mckay "Aspirin-triggered lipoxin enhances macrophage phagocytosis of bacteria while inhibiting inflammatory cytokine production" Am J Physiol Gastrointest Liver Physiol 301: G487-G497, 2011.
Schwab, et al. "Resolvin E1 and protectin D1 activate inflammation-resolution programmes" Nature, vol. 447, Jun. 14, 2007, 869-875.
Serhan, C. "Novel N ω 3-derived local mediators in anti-inflammation and resolution" Pharmacology & Therapeutics 105 (2005) 7-21.
Serhan, C., Novel Pro-Resolving Lipid Mediators in Inflammation Are Leads for Resolution Physiology, Nature. Jun. 5, 2014; 510(7503): 92-101.
Serhan, et al., Novel Functional Sets of Lipid-derived Mediators with Antiinflammatory Actions Generated from Omega-3 Fatty Acids via Cyclooxygenase 2-Nonsteroidal Antiinflammatory Drugs and Transcellular Processing, J. Exp. Med., vol. 192, No. 8, Oct. 16, 2000 1197-1204.

(Continued)

Primary Examiner — Barbara P Badio
(74) Attorney, Agent, or Firm — Edwin S. Flores; Daniel J. Chalker; Chalker Flores, LLP

(57) ABSTRACT

The present invention includes a composition and method of producing aspirin in situ, the method comprising: identifying a subject in need of aspirin or aspirin-like compounds; and providing the subject with a composition comprising: a source of methyl salicylate, an acetyl donor, and L-Arginine, wherein the composition is effective to produce aspirin-triggered resolvins in the subject without the deleterious effect of the aspirin or aspirin-like compounds in the stomach.

7 Claims, 1 Drawing Sheet

(56) References Cited

OTHER PUBLICATIONS

Serhan, et al., Novel Proresolving Aspirin-Triggered DHA Pathway, Chemistry & Biology 18, 976-987, Aug. 26, 2011.
Serhan, et al., Resolvins: A Family of Bioactive Products of Omega-3 Fatty Acid Transformation Circuits Initiated by Aspirin Treatment that Counter Proinflammation Signals, J. Exp. Med., vol. 196, No. 8, Oct. 21, 2002 1025-1037.
Skarke, et al. "Bioactive products formed in humans from fish oils" J. of Lipid Research, Sep. 29, 2015, pp. 1-42.
Sok, et al. "Aspirin-triggered resolvin D1-modified materials promote the accumulation of pro-regenerative immune cell subsets and enhance vascular remodeling" Acta Biomaterialia (2017), 1-34.
United States Patent & Trademark Office, International Search Report and Written Opinion of the International Searching Authority for PCT/US2018/027314 dated Jun. 18, 2018, 7 pp.
Xu, et al. "Resolvins RvE1 and RvD1 attenuate inflammatory pain via central and peripheral actions" Nature Medicine, vol. 16, No. 5, May 2010, 592-598.

PRODUCTION OF ASPIRIN-TRIGGERED RESOLVINS WITHOUT THE USE OF ASPIRIN IN A DIETARY OMEGA-3 SUPPLEMENT

CROSS-REFERENCE TO RELATED APPLICATIONS

This patent application is a divisional of U.S. patent application Ser. No. 15/951,755 filed on Apr. 12, 2018 entitled "Production of Aspirin Triggered Resolvins Without the Use of Aspirin in a Dietary Omega-3 Supplement," which claims priority to U.S. provisional patent application Ser. No. 62/484,676 filed on Apr. 12, 2017 entitled "Production of Aspirin Triggered Resolvins Without the Use of Aspirin in a Dietary Omega-3 Supplement," all of which is hereby incorporated by reference in their entirety.

STATEMENT OF FEDERALLY FUNDED RESEARCH

Not applicable.

TECHNICAL FIELD OF THE INVENTION

The present invention relates in general to the field of aspirin, and more particularly, to a novel compositions and methods for producing aspirin in situ without the deleterious side effects of aspirin in the stomach.

BACKGROUND OF THE INVENTION

Without limiting the scope of the invention, its background is described in connection with aspirin.

One such patent is U.S. Pat. No. 8,586,073, issued to Drapeau, et al., entitled "Methods and formulations for administration of resolvin anti-inflammatory compounds". These inventors are said to teach resolvins and their use as anti-inflammatory compounds. The resolvins can be administered in a variety of forms, including drug depots comprising polymers or lipids. The pharmaceutical formulations with resolvins are said to be used to treat a variety of conditions including acute pain and chronic pain.

Another such patent is U.S. Pat. No. 7,341,840, issued to Serhan, et al., entitled "Methods for identification and uses of anti-inflammatory receptors for eicosapentaenoic acid analogs". These inventors are said to teach methods for the identification and uses of receptors that interact with anti-inflammatory compounds derived from eicosapentaenoic acid (EPA). The receptors are of the G-protein coupled receptor (GPCR) family, and are said to be useful for screening candidate substances for anti-inflammatory activity, especially substances that are analogs of EPA. Such analogs are termed "resolvins"; and are typically di- and tri-hydroxy EPA analogs.

SUMMARY OF THE INVENTION

In one embodiment, the present invention includes a method of producing aspirin or aspirin-like molecule in situ, the method comprising: identifying a subject in need of aspirin or aspirin-like compounds; and providing the subject with a composition comprising: a source of methyl salicylate, an acetyl donor, and L-Arginine, wherein the composition is effective to produce aspirin-triggered resolvins in the subject without the deleterious effect of the aspirin or aspirin-like compounds in the stomach. The skilled artisan will recognize that once in the body, the compounds of the present invention will undergo a variety of chemical reactions, under varying reaction conditions, and/or in the presence of enzymes and other chemical modifying agents that may lead to the formation of aspirin or other aspirin-like compounds, which effect can be measured in the form of pain killing or other known activities of aspirin and aspirin-like compounds. In one aspect, the source of methyl salicylate is wintergreen oil or eastern teaberry oil. In another aspect, the source of methyl salicylate is a *Gaultheria* sp., *Betula* sp., *Spiraea* sp. or a *Polygala* sp. In another aspect, the methyl salicylate is provided in an amount between 10 mg and 60 mg. In another aspect, the acetyl donor is provided in an amount between 30 mg and 300 mg. In another aspect, the L-Arginine is provided in an amount between 3 mg and 40 mg. In another aspect, the method further comprises packaging the composition into a gelcap, tablet, powder, cream, lotion, liquid, softgel, poultice, suppository, or serum. In another aspect, the method further comprises formulating the composition for oral, sublingual, subcutaneous, percutaneous, intramuscular, nasal, intradermal, pulmonary, intraalveolar, intravaginal, intrarectal, intraperitoneal or intravenous administration. In another aspect, the composition demonstrates increase potency and reduced off-target effects when compared to aspirin, aspirin-like products, or taken separately. In another aspect, the acetyl donor is d,1-alpha-Tocopherol Acetate, Vitamin E, or an acetylated vitamin. In another aspect, the method further comprises adding an Omega-3 dietary supplement to the composition. In another aspect, the method further comprises adding eicosapentaenoic acid (EPA) to the composition. In another aspect, the method further comprises adding docosahexaenoic acid (DHA) to the composition. In another aspect, the composition comprises an emulsifier selected from beeswax, ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, sodium lauryl sulfate, and combinations thereof. In another aspect, the composition comprises one or more buffering agents.

In another embodiment, the present invention includes a nutritional supplement comprising: a composition comprising a source of methyl salicylate, an acetyl donor, and L-Arginine, wherein the composition is effective to produce aspirin-triggered resolvins in the subject without the deleterious effect of the aspirin or aspirin-like compounds in the stomach. In one aspect, the source of methyl salicylate is wintergreen oil or eastern teaberry oil. In another aspect, the source of methyl salicylate is a *Gaultheria* sp., *Betula* sp., *Spiraea* sp. or a *Polygala* sp. In another aspect, the methyl salicylate is provided in an amount between 10 mg and 60 mg. In another aspect, the acetyl donor is provided in an amount between 30 mg and 300 mg. In another aspect, the L-Arginine is provided in an amount between 3 mg and 40 mg. In another aspect, the composition is provided in a gelcap, tablet, powder, cream, lotion, liquid, softgel, poultice, suppository, or serum. In another aspect, the composition is formulated for oral, sublingual, subcutaneous, percutaneous, intramuscular, nasal, intradermal, pulmonary, intraalveolar, intravaginal, intrarectal, intraperitoneal or intravenous administration. In another aspect, the composition demonstrates increased potency and reduced off-target effects when compared to aspirin, aspirin-like products, or taken separately. In another aspect, the acetyl donor is d,1-alpha-Tocopherol Acetate, Vitamin E, or an acetylated vitamin. In another aspect, the composition further comprises an Omega-3 dietary supplement to the composition.

In another aspect, the composition further comprises an eicosapentaenoic acid (EPA) to the composition. In another aspect, the composition further comprises a docosahexaenoic acid (DHA) to the composition. In another aspect, the composition comprises an emulsifier selected from beeswax, ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, sodium lauryl sulfate, and combinations thereof. In another aspect, the composition comprises one or more buffering agents.

In another embodiment, the present invention includes a nutritional supplement comprising: a source of methyl salicylate, an acetyl donor, and L-Arginine, wherein the composition is effective to produce aspirin-triggered resolvins in the subject without the deleterious effect of the aspirin or aspirin-like compounds in the stomach.

In another embodiment, the present invention includes a nutritional supplement consists essentially of: a source of methyl salicylate, an acetyl donor, and L-Arginine, wherein the composition is effective to produce aspirin-triggered resolvins in the subject without the deleterious effect of the aspirin or aspirin-like compounds in the stomach.

In another embodiment, the present invention includes a nutritional supplement consists of: a source of methyl salicylate, an acetyl donor, and L-Arginine, wherein the composition is effective to produce aspirin-triggered resolvins in the subject without the deleterious effect of the aspirin or aspirin-like compounds in the stomach.

In another embodiment, the present invention includes a nutritional supplement comprising: methyl salicylate, d,1-alpha-Tocopherol Acetate, Vitamin E, or an acetylated vitamin, L-Arginine, eicosapentaenoic acid (EPA) and docosahexaenoic acid (DHA), wherein the supplement is effective to produce aspirin-triggered resolvins in the subject without the deleterious effect of the aspirin or aspirin-like compounds in the stomach.

In another embodiment, the present invention includes a nutritional supplement consisting essentially of: methyl salicylate, d,1-alpha-Tocopherol Acetate, Vitamin E, or an acetylated vitamin, L-Arginine, eicosapentaenoic acid (EPA) and docosahexaenoic acid (DHA), wherein the supplement is effective to produce aspirin-triggered resolvins in the subject without the deleterious effect of the aspirin or aspirin-like compounds in the stomach.

In another embodiment, the present invention includes a nutritional supplement consists of: methyl salicylate, d,1-alpha-Tocopherol Acetate, Vitamin E, or an acetylated vitamin, L-Arginine, eicosapentaenoic acid (EPA) and docosahexaenoic acid (DHA), wherein the supplement is effective to produce aspirin-triggered resolvins in the subject without the deleterious effect of the aspirin or aspirin-like compounds in the stomach.

In another embodiment, the present invention includes a method of treating a subject in need for pain relief or improved cardiovascular function comprising: identifying a subject in need of aspirin or aspirin-like compounds; and providing the subject with a supplement comprising: a source of methyl salicylate, an acetyl donor, and L-Arginine, wherein the composition is effective to produce aspirin-triggered resolvins in the subject without the deleterious effect of the aspirin or aspirin-like compounds in the stomach. In one aspect, the source of methyl salicylate is wintergreen oil or eastern teaberry oil. In another aspect, the source of methyl salicylate is a *Gaultheria* sp., *Betula* sp., *Spiraea* sp. or a *Polygala* sp. In another aspect, the methyl salicylate is provided in an amount between 10 mg and 60 mg. In another aspect, the acetyl donor is provided in an amount between 30 mg and 300 mg. In another aspect, the L-Arginine is provided in an amount between 3 mg and 40 mg. In another aspect, the method further comprises packaging the composition into a gelcap, tablet, powder, cream, lotion, liquid, softgel, poultice, suppository, or serum. In another aspect, the method further comprises formulating the composition for oral, sublingual, subcutaneous, percutaneous, intramuscular, nasal, intradermal, pulmonary, intraalveolar, intravaginal, intrarectal, intraperitoneal or intravenous administration. In another aspect, the composition demonstrates increase potency and reduced off-target effects when compared to aspirin, aspirin-like products, or taken separately. In another aspect, the acetyl donor is d,1-alpha-Tocopherol Acetate, Vitamin E, or an acetylated vitamin. In another aspect, the method further comprises adding an Omega-3 dietary supplement the composition.

In another aspect, the method further comprises adding eicosapentaenoic acid (EPA) to the composition. In another aspect, the method further comprises adding docosahexaenoic acid (DHA) to the composition. In another aspect, the composition comprises an emulsifier selected from beeswax, ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, sodium lauryl sulfate, and combinations thereof. In another aspect, the composition comprises one or more buffering agents.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
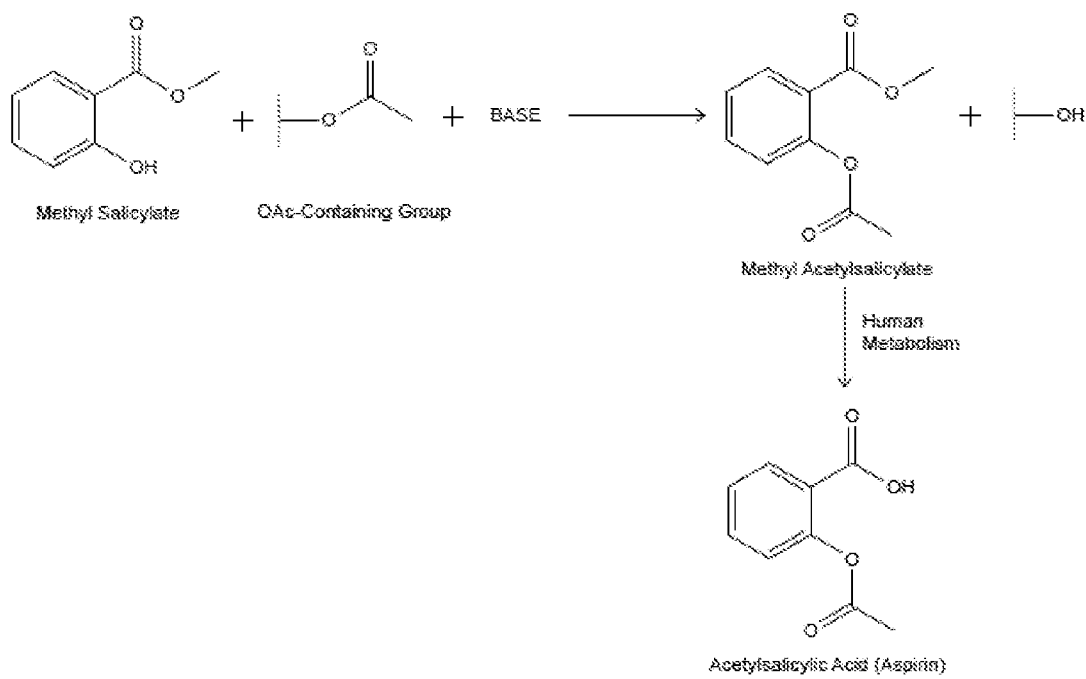
FIG. 1 shows the basic equation for the generation of aspirin in-situ based on simple principles of organic chemistry of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The invention described herein relates to a novel method to generate aspirin and aspirin-like compounds in situ from readily available and regulatory compliant materials used in the nutraceutical industry. This methodology is incorporated into a fish oil nutritional supplement in order to produce Aspirin-Triggered Resolvins in the body without the use of aspirin. This new method has the advantages of ease of use, regulatory compliance in the supplement industry, and increased conversion of Aspirin-Triggered Resolvins due to the proximity effect of having these ingredients all in the same formulation. This is the first work to describe a method to create Aspirin-Triggered Resolvins directly in the body without the use of Aspirin and all in one simple formulation.

Polyunsaturated fatty acids (PUFAs) from fish oil have demonstrated a profound ability to maintain human health from a myriad of different mechanisms. Among the PUFAs in fish oil, eicosapentaenoic acid (EPA) and docosahexaenoic acid (DHA) are the major bioactive players. Research over the last 15 years has shown that EPA and DHA are actually prodrugs in the body; their biological activity in vivo is due to the production of potent anti-inflammatory metabolites called Resolvins (Rv) and Protectins (PD). Different Resolvins and Protectins with varying degrees of anti-inflammatory properties are produced from both EPA and DHA.

Hundreds of clinical studies have been conducted over the years showing the health benefits of EPA and DHA-containing omega-3 supplements for maintaining cardio health and healthy inflammatory status in the body. Meta-analysis of these studies demonstrates that study outcomes are more effective and significant when participants concurrently take a low-regiment dose of acetylsalicylic acid (aspirin). Recent research has shown that the increased anti-inflammatory properties of taking an omega-3 supplement in the presence of a low dose of aspirin is due to the acetylation of the cyclooxygenase-2 (COX-2) enzyme which results in the enzymatic conversion of EPA and DHA into a new class of Resolvins known as Aspirin-Triggered Resolvins (AT-Rv) that possess even greater anti-inflammatory properties than Resolvins not triggered by aspirin.

The problem with taking aspirin and an EPA/DHA-containing nutritional supplement separately is the chance for off-target effects due to the metabolism of aspirin, EPA, and DHA before they have the chance to react with each other in the gut. This invention helps to circumvent this situation and increase the effectiveness of the conversion of aspirin, EPA, and DHA to Aspirin-Triggered Resolvins.

Dosage Forms.

A dosage unit for use of the composition of the present invention may be mixed together, form ionic or even covalent bonds. The methyl salicylate, d,1-alpha-Tocopherol Acetate, and L-Arginine of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the methyl salicylate, d,1-alpha-Tocopherol Acetate, and L-Arginine of the present invention to a patient in need of therapy. The methyl salicylate, d,1-alpha-Tocopherol Acetate, and L-Arginine may also be administered as any one of known salt forms.

Methyl salicylate, d,1-alpha-Tocopherol Acetate, and L-Arginine can be administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the methyl salicylate, d,1-alpha-Tocopherol Acetate, and L-Arginine may be formulated to provide, e.g., maximum and/or consistent dosing for the particular form for oral, rectal, topical, intravenous injection or parenteral administration. While the methyl salicylate, d,1-alpha-Tocopherol Acetate, and L-Arginine may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, the methyl salicylate, d,1-alpha-Tocopherol Acetate, and L-Arginine may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

Methyl salicylate, d,1-alpha-Tocopherol Acetate, and L-Arginine may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

Methyl salicylate, d,1-alpha-Tocopherol Acetate, and L-Arginine may also be coupled to one or more soluble, biodegradable, bioacceptable polymers as drug carriers or as a prodrug. Such polymers may include: polyvinylpyrrolidone, pyran copolymer, polyhydroxypropylmethacrylamide-phenol, polyhydroxyethylasparta-midephenol, or polyethyleneoxide-polylysine substituted with palmitoyl residues, mixtures thereof, and the like. Furthermore, the methyl salicylate, d,1-alpha-Tocopherol Acetate, and L-Arginine may be coupled one or more biodegradable polymers to achieve controlled release of the methyl salicylate, d,1-alpha-Tocopherol Acetate, and L-Arginine, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the methyl salicylate, d,1-alpha-Tocopherol Acetate, and L-Arginine and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfate, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propylparaben, and/or chlorobutanol. Suitable pharmaceutical carriers are described in Remington's Pharmaceutical Sciences, Mack Publishing Company, a standard reference text in this field, relevant portions incorporated herein by reference.

For direct delivery to the nasal passages, sinuses, mouth, throat, esophagus, trachea, lungs and alveoli, the methyl salicylate, d,1-alpha-Tocopherol Acetate, and L-Arginine may also be delivered as an intranasal form via use of a suitable intranasal vehicle. For dermal and transdermal delivery, the methyl salicylate, d,1-alpha-Tocopherol Acetate, and L-Arginine may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of methyl salicylate, d,1-alpha-Tocopherol Acetate, and L-Arginine may include the following forms.

Capsules. Capsules may be prepared by filling standard two-piece hard gelatin capsules each with 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet with the methyl salicylate, d,1-alpha-Tocopherol Acetate, and L-Arginine, appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the active ingredient is compressed into a hardness in the range 6 to 12 Kp. The hardness of the final tablets is influenced by the linear roller compaction strength used in preparing the granules or granulates, which are influenced by the particle size of, e.g., the monosodium hydrogen carbonate and sodium hydrogen carbonate.

For smaller particle sizes, a linear roller compaction strength of about 15 to 20 KN/cm may be used.

Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

The composition of methyl salicylate, d,1-alpha-Tocopherol Acetate, and L-Arginine may be formulated for release that is immediate, rapid, extended, bi-phasic, etc. By "immediate release" is meant a release of an active agent to an environment over a period of seconds to no more than about 30 minutes once release has begun and release begins within no more than about 2 minutes after administration. An immediate release does not exhibit a significant delay in the release of drug. By "rapid release" is meant a release of an active agent to an environment over a period of 1-59 minutes or 0.1 minute to three hours once release has begun and release can begin within a few minutes after administration or after expiration of a delay period (lag time) after administration. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms). By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. The term "controlled release", as regards to drug release, includes the terms "extended release", "prolonged release", "sustained release", or "slow release", as these terms are used in the pharmaceutical sciences. An controlled release can begin within a few minutes after administration or after expiration of a delay period (lag time) after administration.

A slow release dosage form is one that provides a slow rate of release of drug so that drug is released slowly and approximately continuously over a period of 3 hours, 6 hours, 12 hours, 18 hours, a day, 2 or more days, a week, or 2 or more weeks, for example.

A timed-release dosage form is one that begins to release drug after a predetermined period of time as measured from the moment of initial exposure to the environment of use.

A targeted release dosage form generally refers to an oral dosage form that designed to deliver drug to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can deliver to other sections of the gastrointestinal tract such as the stomach, jejunum, ileum, duodenum, cecum, large intestine, small intestine, colon, or rectum.

By "delayed release" it is meant that initial release of drug occurs after expiration of an approximate delay (or lag) period. For example, if release of drug from an extended release composition is delayed two hours, then release of drug from begins at about two hours after administration of the composition, or dosage form, to a subject. In general, a delayed release is opposite an immediate release, wherein release of drug begins after no more than a few minutes after administration. Accordingly, the drug release profile from a particular composition can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

A pulsatile release dosage form is one that provides pulses of high active ingredient concentration, interspersed with low concentration troughs. A pulsatile profile containing two peaks may be described as "bimodal" or "biphasic".

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

The resulting product may also be formulated to exhibit enhanced dissolution rate of a formulated poorly water soluble drug.

The present invention includes, but is not limited to, the following: (1) a method for producing aspirin both in vivo and in situ through the use of simple commercially available starting materials. (2) A method using wintergreen oil (a source of Methyl Salicylate), d,1-alpha-Tocopherol Acetate, and L-Arginine. (3) Coupling this in situ aspirin-generating method with EPA/DHA-containing fish oil to produce Aspirin-Triggered Resolvins in the body all in a single delivery form, and without the need for taking aspirin separately. (4) This aspirin-generating methodology is used in this case with a EPA/DHA containing fish oil but could also be used either by itself or with other compounds known to have a beneficial effect when take concurrently with aspirin.

In addition to wintergreen oil, vitamin E acetate, and L-arginine, other in ingredients are EPA, and/or DHA. The aspirin-generation composition and methods described herein can be used separately in a nutritional supplement to generate aspirin in the body. This composition and methods taught herein use common nutritional ingredients approved by global regulatory agencies for use in nutritional/dietary supplements. The composition and methods trigger the in situ generation of aspirin in the same formulation as EPA and DHA might increase potency and reduce off-target effects that are generated when taken separately. This formulation can be made in a soft gel delivery form with beeswax used as an emulsifier in order to increase solubility and material uniformity. The composition and methods for in situ aspirin-formation could also be applied in powder, tablet, cream, lotion, and liquid delivery forms. The composition and methods for in situ aspirin-generation can also be applied to any application wherein the generation of aspirin would be beneficial to human health.

FIG. 1 shows the basic equation for the generation of aspirin in situ based on simple principles of organic chemistry is shown in. The first step in this process is selection of a base that can deprotonate the phenolic hydrogen of methyl salicylate (which is the major component of, e.g., wintergreen oil). The pKa of this hydrogen is going to be lower than the usual number of 10 for phenolic alcohols due to the additional stabilization of the ester group on the aromatic ring. As such, a relatively weak base (like the amine of L-arginine) should be able to deprotonate the phenolic hydrogen to the alkoxide. The next step in the reaction is to add a natural compound that is an acetyl donor and regulatory compliant in the nutraceutical industry. Acetyl derivatives of common vitamins (like d,1-alpha-tocopherol acetate) are one choice. The mechanism of this reaction involves deprotonation of the phenolic hydrogen by the base to form the alkoxide. Next, the nucleophilic alkoxide would attack the carbonyl carbon of the acetyl group on the donor molecule, which, upon formation and collapse of the tetrahedral intermediate, provides methyl acetylsalicylate and an alcohol as a byproduct. The ester group of methyl acetylsalicylate is cleaved in vivo by many esterase enzymes in the body to yield aspirin.

Figure 2:
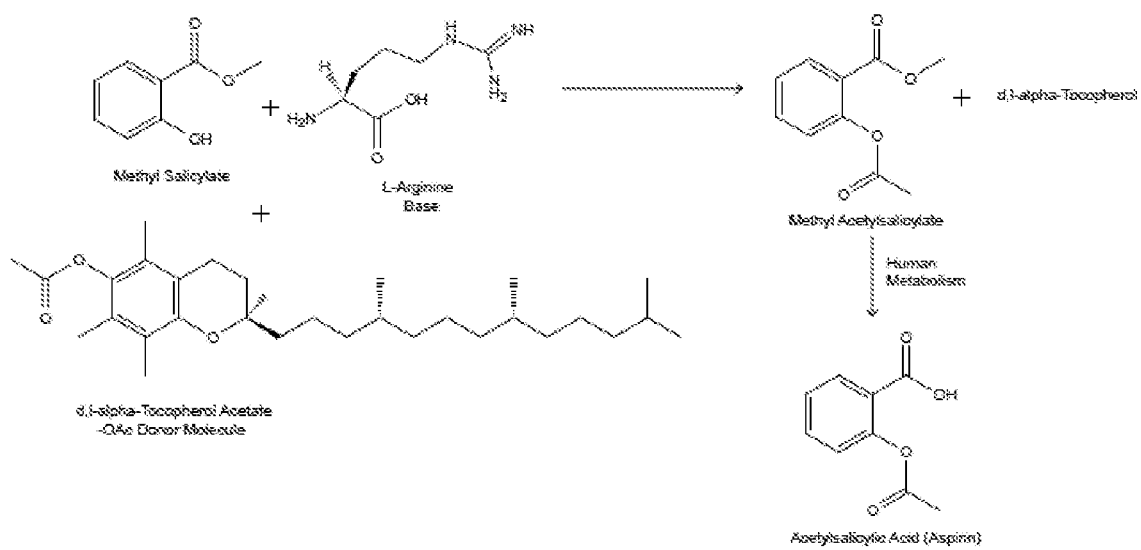
FIG. 2 shows a specific example of an in-situ aspirin-generating reaction.

FIG. 2 shows one example of specific ingredients for this aspirin-generating reaction. Wintergreen oil is mostly comprised of methyl salicylate and is one starting material of choice due to its allowed regulatory status, cheap price, plentiful supply chain, and striking similarity in chemical structure to aspirin. The base used in the example below is the free base form of L-arginine—which is also widely available and used in the nutritional supplement industry. Vitamin E acetate is used as the acetyl donor due to the labile nature of the acetyl group and also due to the wide acceptability of Vitamin E in the nutraceutical industry. The benefit of using L-Arginine and Vitamin E in this reaction is the additional health functional benefits of these ingredients in addition to the in situ generation of aspirin.

As such, the present invention includes a novel method for the in situ formation of aspirin or aspirin-like products in the body from readily available starting materials in the nutraceutical industry. This in situ aspirin or aspirin-like product generation method can been added to a Omega-3 dietary supplement in order to convert EPA and DHA in fish oil into a class of compounds called Aspirin-Triggered Resolvins that possess potent anti-inflammatory activity and are key class of compounds responsible for the clinically-validated biological activity of omega-3 supplementation.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Groeger, et al., Cyclooxygenase-2 generates anti-inflammatory mediators from omega-3 fatty acids, NATURE CHEMICAL BIOLOGY, Vol. 6, June 2010, 433-441.

Serhan, et al., Resolvins: A Family of Bioactive Products of Omega-3 Fatty Acid Transformation Circuits Initiated by Aspirin Treatment that Counter Proinflammation Signals, J. Exp. Med., Volume 196, Number 8, Oct. 21, 2002 1025-1037.

Dalli, et al., Resolvin D3 and Aspirin-Triggered Resolvin D3 Are Potent Immunoresolvents, Chemistry & Biology 20, 188-201, Feb. 21, 2013.

Serhan, et al., Novel Proresolving Aspirin-Triggered DHA Pathway, Chemistry & Biology 18, 976-987, Aug. 26, 2011.

Serhan, et al., Novel Functional Sets of Lipid-derived Mediators with Antiinflammatory Actions Generated from Omega-3 Fatty Acids via Cyclooxygenase 2-Nonsteroidal Antiinflammatory Drugs and Transcellular Processing, J. Exp. Med., Volume 192, Number 8, Oct. 16, 2000 1197-1204.

Chen, C., COX-2's new role in inflammation, NATURE CHEMICAL BIOLOGY, Vol 6, June 2010, 401-402.

Serhan, C., Novel Pro-Resolving Lipid Mediators in Inflammation Are Leads for Resolution Physiology, Nature. Jun. 5, 2014; 510(7503): 92-101.

Xu, et al., Resolvins RvE1 and RvD1 attenuate inflammatory pain via central and peripheral actions, NATURE MEDICINE, Volume 16, Number 5, May 2010, 592-598.

Morris, et al., Effects of Low-Dose Aspirin on Acute Inflammatory Responses in Humans, J Immunol 2009; 183: 2089-2096; 13 Jul. 2009.

Serhan, C., Novel N w 3-derived local mediators in anti-inflammation and resolution, Pharmacology & Therapeutics 105 (2005) 7-21.

Schwab, et al., Resolvin E1 and protectin D1 activate inflammation-resolution programmes, Nature, Vol 447, 14 Jun. 2007, 869-875.

Ariota, et al., Stereochemical assignment, anti-inflammatory properties, and receptor for the omega-3 lipid mediator resolvin E1, J. Exp. Med., Vol. 201, No. 5, Mar. 7, 2005 713-722.

Buckley, et al., Proresolving Lipid Mediators and Mechanisms in the Resolution of Acute Inflammation, Immunity 40, Mar. 20, 2014, 315-327.

Ogata, et al., Effects of aspirin-triggered resolvin D1 on peripheral blood mononuclear cells from patients with Chagas' heart disease, European Journal of Pharmacology 777 (2016) 26-32.

Lima-Garcia, et al., The precursor of resolvin D series and aspirin-triggered resolvin D1 display anti-hyperalgesic properties in adjuvant-induced arthritis in rats, British Journal of Pharmacology (2011) 164 278-293.

Kohli, Resolvins and protectins: mediating solutions to inflammation, British Journal of Pharmacology (2009), 158, 960-971.

Prescott and McKay, Aspirin-triggered lipoxin enhances macrophage phagocytosis of bacteria while inhibiting inflammatory cytokine production, Am J Physiol Gastrointest Liver Physiol 301: G487-G497, 2011.

Skarke, et al., Bioactive products formed in humans from fish oils, J. of Lipid Research, Sep. 29, 2015, pages 1-42.

Sok, et al., Aspirin-triggered resolvin D1-modified materials promote the accumulation of pro-regenerative immune cell subsets and enhance vascular remodeling, Acta Biomaterialia (2017), 1-34.

What is claimed is:

1. A method of treating a subject in need of pain relief or aspirin-triggered resolvins cardiovascular function comprising:
    identifying a subject in need of aspirin; and
    providing the subject with a composition comprising a source of methyl salicylate selected from an oil from a *Gaultheria* sp., *Betula* sp., *Spiraea* sp. or a Polygala sp., an acetyl donor selected from d,1-alpha-Tocopherol Acetate, or an acetylated vitamin, and L-Arginine, wherein the composition is effective to produce aspirin-triggered resolvins in the subject without the deleterious effect of the aspirin or aspirin-triggered resolvins in the stomach of the subject.

2. The method of claim 1, wherein the source of methyl salicylate is wintergreen oil or eastern teaberry oil.

3. The method of claim 1, wherein the at least one of: the methyl salicylate is provided in an amount between 10 mg and 60 mg, the acetyl donor is provided in an amount between 30 mg and 300 mg, or the L-Arginine is provided in an amount between 3 mg and 40 mg.

4. The method of claim 1, further comprising packaging the composition into a gelcap, tablet, powder, cream, lotion, liquid, softgel, poultice, suppository, or serum.

5. The method of claim 1, further comprising formulating the composition for oral, sublingual, subcutaneous, percutaneous, intramuscular, nasal, intradermal, pulmonary, intraalveolar, intravaginal, intrarectal, intraperitoneal or intravenous administration.

6. The method of claim 1, further comprising adding at least one of:
    an Omega-3 dietary supplement, an eicosapentaenoic acid (EPA), a docosahexaenoic acid (DHA), or one or more buffering agents.

7. The method of claim 1, wherein the composition further comprises an emulsifier selected from beeswax, ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, sodium lauryl sulfate, and combinations thereof.

* * * * *